United States Patent [19]

Hamilton et al.

[11] Patent Number: 5,414,123
[45] Date of Patent: May 9, 1995

[54] POLYETHER COMPOUNDS HAVING BOTH IMINE AND HYDROXYL FUNCTIONALITY AND METHODS OF SYNTHESIS

[75] Inventors: R. Scott Hamilton, Bear River City; Gary K. Lund, Ogden; Robert M. Hajik, Willard, all of Utah

[73] Assignee: Thiokol Corporation, Ogden, Utah

[21] Appl. No.: 173,425

[22] Filed: Dec. 23, 1993

Related U.S. Application Data

[63] Continuation-in-part of Ser. No. 943,918, Sep. 11, 1992, abandoned.

[51] Int. Cl.$^6$ .............................................. C07C 251/24
[52] U.S. Cl. .................................. 564/275; 564/273
[58] Field of Search ................................. 564/273, 275

[56] References Cited

U.S. PATENT DOCUMENTS

| | | | |
|---|---|---|---|
| 2,300,998 | 11/1942 | White et al. | 260/566 |
| 3,110,732 | 11/1963 | Speranza et al. | 564/275 |
| 3,489,565 | 1/1970 | Kohn | 96/66 |
| 3,790,416 | 3/1974 | Dehm | 149/19 |
| 3,827,780 | 8/1974 | Labes | 350/160 LC |
| 3,891,709 | 6/1975 | Higuchi et al. | 260/584 B |
| 4,000,023 | 12/1976 | Oberth et al. | 149/19.4 |
| 4,016,113 | 4/1977 | Preston et al. | 260/2.5 AM |
| 4,019,933 | 4/1977 | Cuksee et al. | 149/19.4 |
| 4,151,317 | 4/1979 | Burba et al. | 427/388 D |
| 4,226,792 | 10/1980 | Tajima | 260/435 A |
| 4,391,660 | 7/1983 | Corley et al. | 149/19.9 |
| 4,402,699 | 9/1983 | Rose et al. | 8/412 |
| 4,410,376 | 10/1983 | Bruenner et al. | 149/19.4 |
| 4,483,741 | 1/1985 | Ducote et al. | 149/19.4 |
| 4,491,538 | 1/1985 | McCoy | 252/541 |
| 4,531,989 | 7/1985 | Ducote et al. | 149/19.2 |
| 4,745,135 | 5/1988 | Thomas et al. | 521/114 |
| 4,789,691 | 12/1988 | Matzke et al. | 521/159 |
| 4,799,980 | 1/1989 | Reed, Jr. | 149/19.4 |
| 4,857,071 | 8/1989 | Anderson | 8/414 |
| 4,909,954 | 3/1990 | Palazzotto | 558/422 |
| 4,915,755 | 4/1990 | Kim | 149/19.4 |
| 4,944,815 | 7/1990 | Consaga | 149/19.1 |
| 4,971,640 | 11/1990 | Chi | 149/19.9 |

OTHER PUBLICATIONS

Nakamura et al., "An Infrared Study of the C=N Stretching Frequency in N-Benzylideneaniline Derivatives", Chem. Pharm. Bull., vol. 15, No. 5, pp. 585–592, 1967.

Reeves et al., "The Protonation of Benzylideneaniline and it's p- and p- Dimethylamino Derivatives", Communication No. 2317 from the Kodak Research Laboratories, Rochester, N.Y., vol. 85, pp. 724–729, Mar. 20, 1963.

Ducote, "Amine Salts as AP Bonding Agents", U.S. Army Missile Command Restone Arsenal, Ala.

*Primary Examiner*—Peter O'Sullivan
*Attorney, Agent, or Firm*—Madson & Metcalf; Ronald L. Lyons

[57] ABSTRACT

Polyether organic compounds are described which have both imine and hydroxyl functionality. These materials are synthesized by reacting a primary amine with an aldehyde or ketone to form a Schiff base. By definition, a Schiff base comprises the reaction product of a primary amine and an aldehyde. In this case, however, unlike conventional Schiff bases, the reaction product possesses both hydroxyl and Schiff base functionality. In one embodiment of the invention, such a product is produced by the reaction of a polyoxyalkyleneamine (Jeffamine) with p-nitrobenzaldehyde and glycidol. The result is a polyether having both hydroxyl and Schiff base functionality. The compounds produced in this manner are particularly useful as bonding agents in the formulation of solid propellants. The bonding agents provide superior performance, while avoiding the problems encountered when using existing bonding agents. The observed superior performance is believed to arise from the ability of the materials to bond within the propellant matrix by means of the hydroxyl groups, and to align with oxidizers, such as ammonium perchlorate, by means of the Schiff bases.

9 Claims, 2 Drawing Sheets

POLYETHER COMPOUNDS HAVING BOTH IMINE AND HYDROXYL FUNCTIONALITY AND METHODS OF SYNTHESIS

RELATED APPLICATION

This application is a continuation-in-part of Applicant's application Ser. No. 07/943,918, now abandoned, filed Sep. 11, 1992 and entitled "Compounds Having Both Imine and Hydroxyl Functionality and Methods of Synthesis," which application is incorporated herein by this reference.

BACKGROUND

1. The Field of the Invention

The present invention relates to polyether organic compounds having both imine and hydroxyl functionality and methods for their synthesis. More particularly, the present invention relates to the synthesis and use of such organic compounds as bonding agents in the preparation of solid propellants.

2. Technical Background

Solid propellants are used extensively in the aerospace industry. Solid propellants have become the preferred method of powering most missiles and rockets for military, commercial, and space applications. Solid rocket motor propellants have become widely accepted because of the fact that they are relatively simple to manufacture and use, and they have excellent performance characteristics. Furthermore, solid propellant rocket motors are generally substantially more simple and reliable than liquid fuel rocket motors. For all of these reasons, it is found that solid rocket propellants are very reliable and economical.

Typical solid rocket motor propellants are formulated using an oxidizing agent, a fuel, and a binder. At times, the binder and the fuel may be the same. In addition to the basic components, it is conventional to add various bonding agents, plasticizers, curing agents, cure catalysts, and other similar materials which aid in the processing and curing of the propellant. A significant body of technology has developed related solely to the processing and curing of solid propellants.

Many types of propellants used in the industry incorporate ammonium perchlorate (AP) as the oxidizer. The ammonium perchlorate is generally incorporated into the propellant in particulate form. In order to hold the propellant in a coherent form, the components of the propellant are bound together by a binder, such as, but not limited to, a hydroxy-terminated polybutadiene (HTPB) binder. Such binders are widely used and commercially available. It has been found that such propellant compositions provide ease of manufacture, relative ease of handling, good performance characteristics, and are at the same time economical and reliable. As a result, this type of propellant has become a standard in the industry.

Propellants are generally required to meet various mechanical and chemical performance criteria in order to be considered acceptable for routine use. For example, it is important that the propellant have desired mechanical characteristics which allow it to be used in a corresponding rocket or missile. It is important, for example, that the propellant flex during use in order to avoid cracking within the propellant grain.

If the propellant cracks, burning within the crack may be experienced during operation of the rocket or missile. Such, burning in a confined area may result in an increased surface area of burning propellant or increased burn rate at a particular location. This increase in the burn rate and surface area can directly result in failure of the rocket motor due to over pressurization or burn through of the casing.

Accordingly, propellants are typically subjected to standardized stress and strain tests. The typical configuration of the propellant sample tested is often referred to as a JANNAF Class C specimen. The shape and size of such specimens are standard in the industry. Such specimens are typically placed in an Instron ® testing apparatus and then loaded in tension until the specimen fails. Data is recorded during such tests and objective measures of stress and strain performance are provided.

In order to make certain that propellant formulations meet the applicable specifications, it is often necessary to employ a bonding agent within the propellant composition. Bonding agents are used in order to help incorporate solid particles into the polymeric binder system. Use of a bonding agent typically improves the stress and strain characteristics of the propellant.

A number of bonding agents are known and conventional. One such bonding agent is Tepanol (tetraethylenepentamine-acrylonitrile glycidol adduct). Tepanol has been found to be useful as a bonding agent, and improves the processing characteristics of the propellant formulation. Tepanol is believed to become chemically linked to the polymeric propellant binder. Tepanol also electrostatically coordinates with the remaining ammonium perchlorate after forming a Tepanol perchlorate salt from an acid/base reaction with ammonium perchlorate. Thus Tepanol aids in binding the ammonium perchlorate particles within the propellant matrix. Tepanol is also inexpensive and readily available.

Tepanol, however, also causes difficulty in the formulation of propellant. Tepanol is relatively basic, and in the presence of ammonium perchlorate produces a significant amount of ammonia. This makes it necessary to conduct propellant mixing steps under vacuum, and to mix for long periods of time in order to substantially remove the produced ammonia. These characteristics of Tepanol result in significant disadvantages, such as long mix time, high labor costs, ammonium perchlorate attrition, and may shorten the service life of the propellant.

An alternative bonding agent is known commercially as HX-752 and is available from 3M. HX-752 is an aziridine having the following general chemical structure:

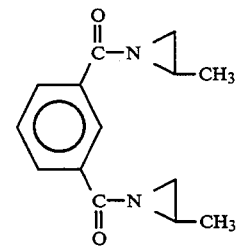

HX-752 is believed to be incorporated into the propellant matrix by ring opening polymerization. HX-752 avoids the production of large amounts of ammonia which plague processes using Tepanol. As a result, some advantages are derived from the use of HX-752.

Even in view of the foregoing, HX-752 is far from ideal as a bonding agent. One significant problem is that of economics. HX-752 presently costs from four to five times as much as Tepanol. Also, the propellant produced when using this material has a relatively high viscosity, which inhibits processing. It is also suspected that HX-752 may be a carcinogen. Thus, it can be seen that the cost and chemical characteristics of HX-752 make it a less than ideal bonding agent.

In summary, conventional bonding agents have significant drawbacks. Tepanol is problematic because of its tendency to produce large quantities of ammonia during propellant mixing and the other limitations mentioned above. Alternative materials, such as HX-752, also present problems including cost and the processing characteristics of the propellant.

Accordingly, it would be an advancement in that art to provide bonding agents which overcame some of the significant limitations encountered using conventional bonding agents. It would be an advancement in the art to provide bonding agents which did not produce significant quantities of ammonia during propellant formulation. It would also be an advancement in the art to provide acceptable alternative bonding agents which were relatively inexpensive. It would also be an advancement in the art to provide such bonding agents which also resulted in propellants having acceptable stress and strain characteristics.

Such compositions and methods are disclosed and claimed herein.

BRIEF SUMMARY AND OBJECTS OF THE INVENTION

The present invention relates to a new class of organic chemical compounds which include both Schiff base functionality and hydroxyl functionality. The compounds of the present invention have the following general structure:

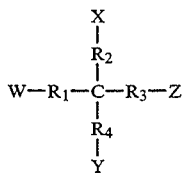

In the general structure, $R_1$, $R_2$, $R_3$, and $R_4$ may be the same or different and are selected from the group consisting of hydrogen or aliphatic linear or branched alkyls having from 1 to 20 carbon atoms, and more preferably from 1 to 10 carbon atoms. At least one of $R_1$, $R_2$, $R_3$, and $R_4$ contains an ether linkage between aliphatic residues. At least one of $R_1$, $R_2$, $R_3$, and $R_4$ contains a hydroxyl group and at least one of $R_1$, $R_2$, $R_3$, and $R_4$ contains a Schiff base (C=N). W, X, Y, and Z are selected from the group consisting of free hydroxyl (—OH), aromatic imine (Schiff base), H, and CH₃. Generally, at least one of W, X, Y, and Z is hydroxyl and at least one is Schiff base. One specific example of a compound falling within the scope of the present invention is:

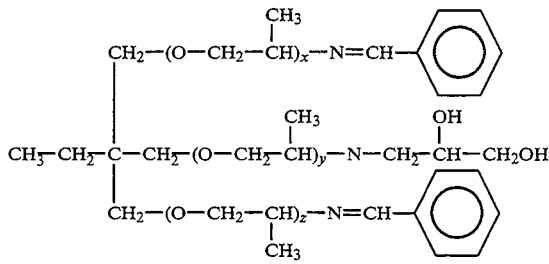

The compounds of the present invention are found to be particularly useful as bonding agents in the formation of propellant compositions; however, the usefulness of this class of materials is not limited to propellant technology. The combination of Schiff base and hydroxyl functionality in a single organic molecule provides the compounds with the ability to serve as effective bonding agents, while avoiding some of the significant problems encountered with conventional materials.

Schiff bases comprise a subgroup of imines. An imine is generally defined as the reaction product of an amine or ammonia and an aldehyde or ketone. This reaction results in a molecule with at least one C=N group. In that context, it has been discovered that unsubstituted imines formed from ammonia are generally unstable and polymerize on standing. Conversely, if a primary amine is used instead of ammonia, a more stable reaction product is formed. This product is defined as a Schiff base. Therefore, as defined herein a Schiff base is an imine (having at least one C=N group) formed by the reaction of a primary amine with an aldehyde or ketone, and preferably in which at least one of the functional residues is aromatic.

It is generally found that aromatic aldehydes or arylamines result in the most stable Schiff. Other aldehydes or ketones may also be used, and Schiff bases formed from such aldehydes or ketones are to be considered to fall within the scope of the present invention.

The primary amine employed may be virtually any amine or —OH containing amine. The amine may be of substantially any carbon chain length and may be branched or unbranched. Other functional groups may also be included on the primary amine molecule, so long as those groups do not interfere with the necessary reaction. Such groups may, for example, include ethers and esters.

In order to provide the desired hydroxyl functionality, the primary amine is also reacted with an epoxide, acrylonitrile, acrylate, methacrylate, or similar molecule capable of imparting hydroxyl functionality to the end product. One such epoxide which provides goods results is glycidol; however, other epoxides are also capable of providing the same desired functionality.

One compound falling within the scope of the present invention is formed by the reaction of polyoxypropylenetriamine (available from Texaco, Co. under the name Jeffamine ®), with p-nitrobenzaldehyde, and glycidol. The product formed from the reaction contains varying amounts of imine and hydroxyl functionality. The reaction is as follows:

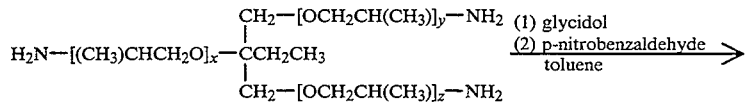

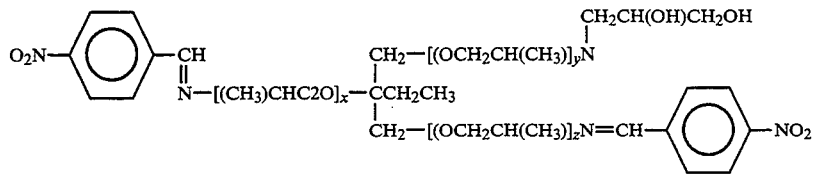

The sum of X+Y+Z could preferably range from about 0 to about 100.

The compounds produced in this manner have been found to constitute effective bonding agents in the formulation of propellant compositions, particularly ammonium perchlorate-based propellants. Using the present invention it is possible to formulate propellants which avoid cracking of the propellant and undesired burning. At that same time the propellants are found to have suitable stress and strain characteristics, and the propellants do not produce excessive quantities of ammonia during mixing.

The compounds of the present invention are believed to result in polar coordination with ammonium perchlorate within the propellant. The N=C group provides a dipole which is sufficient to associate with the ammonium perchlorate. At the same time, the existence of isocyanate reactive functional groups (hydroxyl groups) provides a ready mechanism for incorporating the bonding agent into the binder polymer matrix.

Accordingly, typical propellants within the scope of the present invention comprise from about 10% to about 20% hydroxyterminated polybutadiene (HTPB) binder; from about 0.1% to about 5.0% of the bonding agents disclosed herein; and from about 50% to about 90% ammonium perchlorate (which may be in multiple particle sizes). Other materials may also be included such as fuels (including aluminum), and curing agents such as isophorone diisocyanate.

BRIEF DESCRIPTION OF THE DRAWINGS

In order that the manner in which the above-recited and other advantages and objects of the invention are obtained, a more particular description of the invention briefly described above will be rendered by reference to the appended drawings. Understanding that these drawings only provide data concerning typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
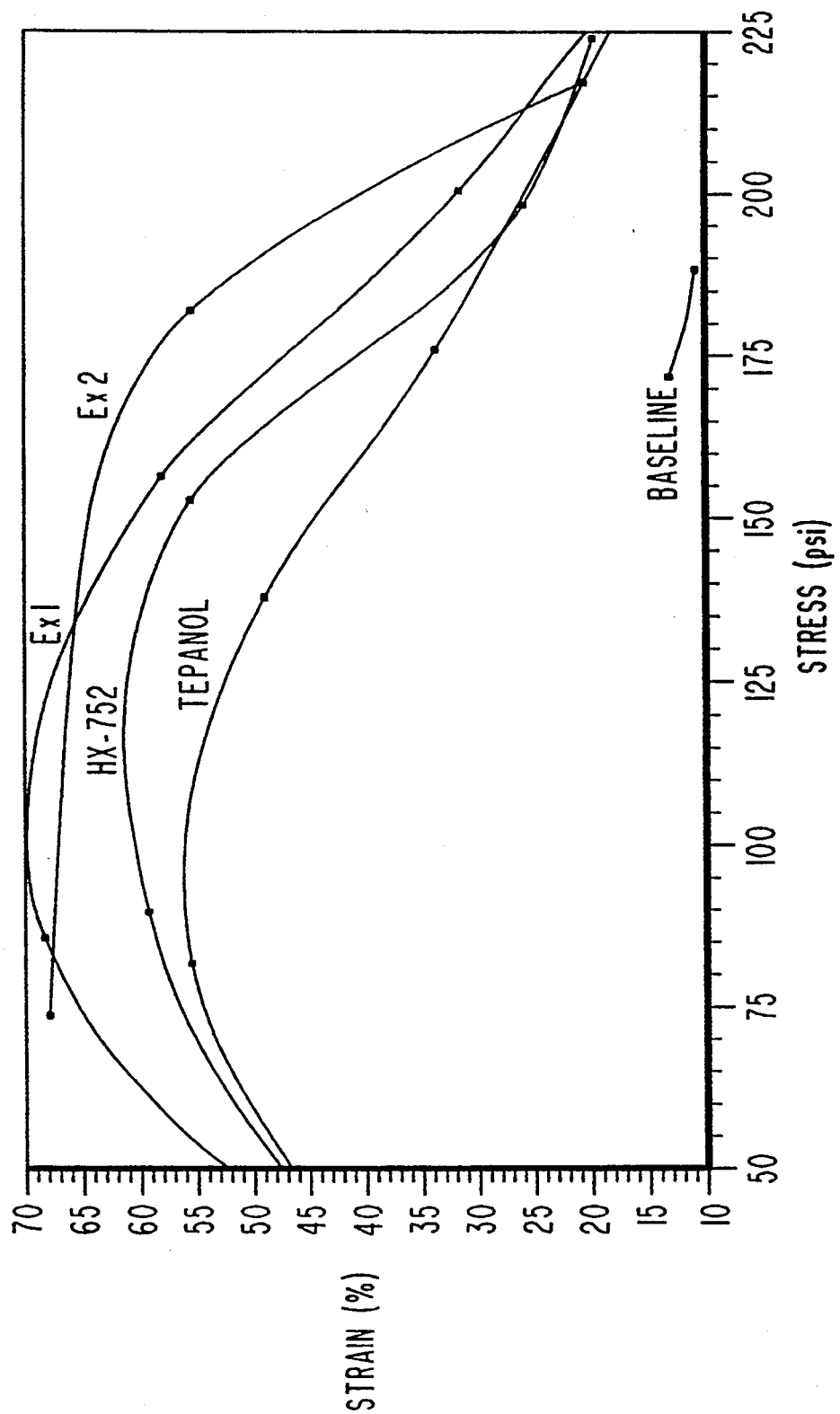
FIG. 1 is a graph which plots stress and strain illustrating baseline data and data from multiple samples.

The present invention is related to organic compounds which have both hydroxyl functionality and at least one Schiff base. The compounds are synthesized by reacting a primary amine with an aldehyde or ketone to form the Schiff base. The amine is also reacted with an epoxide, acrylonitrile, acrylate, methacrylate, or other reagent capable of providing hydroxyl functionality. In certain preferred embodiments it is desirable that the ratio of Schiff base to hydroxyl functionality in the final product be in the range of from about 1 to about 3.

The compounds of the present invention have the following general structure:

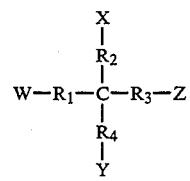

As mentioned above, in the general structure, $R_1$, $R_2$, $R_3$, and $R_4$ may be the same or different and are selected from the group consisting of hydrogen or aliphatic linear or branched alkyls having from 1 to 20 carbon atoms. At least one of $R_1$, $R_2$, $R_3$, and $R_4$ contains an ether linkage between aliphatic residues. At least one of $R_1$, $R_2$, $R_3$, and $R_4$ contains a hydroxyl group and at least one of $R_1$, $R_2$, $R_3$, and $R_4$ contains a Schiff base (C=N). W, X, Y, and Z are selected from the group consisting of free hydroxyl (—OH), aromatic imine (Schiff base), H or $CH_3$. Preferably at least one is hydroxyl and at least one is Schiff base.

One specific example of a compound falling within the scope of the present invention is:

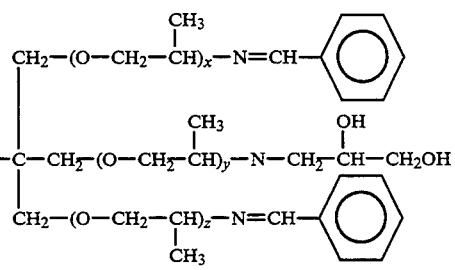

In one exemplary embodiment of the present invention, such a compound is made by reacting Jeffamine ® with p-nitrobenzaldehyde and glycidol. As mentioned above, the use of an aromatic aldehyde or ketone results in a more stable and usable compound. In a typical embodiment of the invention, about 1 mole of Jeffamine T-403 (available commercially from Texaco), is combined with from about 1 to about 3 moles of p-nitrobenzaldehyde, and up to about 3 moles of glycidol.

The reaction may occur in toluene or any other solvent that will allow the reaction to proceed. A water by-product is produced during the synthesis and water may be removed from the reaction mixture by known techniques. For example, azeotropes or drying agents, such has calcium chloride, have been found to be suitable for water removal.

The reaction product is not necessarily uniform, but this fact does not detract from the usefulness of the product. For example, the reacted mixture may include a small percentage of unreacted Jeffamine molecules, along with mono-, di-, and tri-imine reaction products. In addition, the reacted mixture may include mono, di-, and tri-dihydroxypropyl products. Such reaction products, however, are clearly desirable for the purposes described herein and fall within the scope of the present invention.

The polyether-hydroxy-imine compounds produced provide significant improvement over conventional bonding agents so long as the reaction mixture contains compounds containing both hydroxyl groups and Schiff bases. For example, it has been found that use of the compounds produced as bonding agents in propellant formulations at levels below 1%, and even in the 0.15% range, has provided excellent propellants. This is true even when the solids within the propellant exceed about 87%.

Use of the compounds of the present invention as bonding agents provides propellant having good mechanical characteristics. In particular, it is found that such propellants have properties similar to those observed using conventional bonding agents, such as Tepanol and HX-752. FIG. 1 is a plot of stress v. strain measurements obtained using the techniques outlined above wherein JANNAF Class C specimens are placed in an Instron ® machine for stress and strain measurements. FIG. 1 shows the performance of a "baseline" propellant which is free of bonding agents. FIG. 1 also provides plots of propellants employing a Tepanol bonding agent, HX-752, and bonding agents within the scope of the present invention.

FIG. 1 illustrates the improvement in mechanical characteristics over baseline when a bonding agent is employed. In addition, FIG. 1 shows that the use of the compounds of the present invention as bonding agents provides mechanical properties comparable to those achieved by Tepanol and HX-752. As will be discussed in further detail below, the compounds of the present invention provide marked improvement in mechanical characteristics, while avoiding problems, such as ammonia production, encountered with conventional bonding agents.

As discussed briefly above, bonding agents are used to link solid particles to the polymer bonding system of a propellant, thus improving the stress and strain properties of the propellant. The present invention teaches the attachment of a polar moiety (imine) to the overall organic molecular structure (such as a Jeffamine structure). It is presently believed that the imine then attracts and aligns with the ammonium perchlorate by means of an electrostatic interaction. This is accomplished by the nature of the Schiff base, i.e. the C=N group has partial charges ($\delta+ - \delta-$) which are sufficient to align with the polar ammonium perchlorate molecule. In addition, the conversion of the amine to an imine substantially eliminates the problem of ammonia production in the formulation of propellants.

The compounds of the present invention also include hydroxyl functionality. The hydroxyl functionality provides a mechanism for incorporation of the bonding agent and solid ammonium perchlorate within the binder matrix. The hydroxyl functionality reacts with the conventional isocyanate curative used in such propellant formulations. Thus, it is possible to incorporate large quantities of solids into the binder, while still maintaining favorable mechanical properties.

The present invention also relates to the propellants formulated using the bonding agents described above. Importantly, the propellants of the present invention are provided with desirable characteristics because of the nature of the inventive bonding agent.

Typical propellants within the scope of the present invention will comprise from about 10% to about 20% binder. The binder may be a hydroxy-terminated polybutadiene (HTPB). One such binder is R-45M, manufactured by ATOCHEM. Added to the binder will be from about 50% to about 90% oxidizer. The oxidizer generally takes the form of solid particulate ammonium perchlorate having varying particle sizes. Typical particle sizes include 400$\mu$, 200$\mu$, and 20$\mu$ particles. It is conventional in propellant formulation to combine ammonium perchlorate particles of multiple sizes.

Added to these materials will be a bonding agent of the type falling within the scope of the invention. The bonding agent will in general comprise from about 0.05% to about 2.0% by weight of the propellant formulation. In addition, the propellant will likely include a curing agent, such as isophorone diisocyanate, which cross-links the HTPB polymer. Other materials may also be added, including additional fuels (such as aluminum), processing aids, and other similar types of additives.

Thus, a new and useful class of organic compounds has been synthesized. These compounds are especially effective as alternative bonding agents in solid propellant formulation. These compounds are economical to produce. These materials are also convenient to use as bonding agents in that they produce relatively small quantities of ammonia during processing. At that same time, these materials are as effective as known bonding agents in improving the mechanical characteristics of the final propellant formulations.

EXAMPLES

The following examples are given to illustrate various embodiments which have been made or may be made in accordance with the present invention. These examples are given by way of example only, and it is to be understood that the following examples are not comprehensive or exhaustive of the many types of embodiments of the present invention which can be prepared in accordance with the present invention.

Example 1

A compound within the scope of the present invention was synthesized and characterized. The reagents used were as follows:

| Material | Grams | Moles/Equiv. |
| --- | --- | --- |
| Jeffamine T-403 | 30.00 | 0.1936 eq. |
| glycidol | 4.74 | 0.064 moles |
| 4-nitrobenzaldehyde | 19.34 | 0.128 moles |

The synthesis occurred in a 300 ml three-neck round bottom flask equipped with a dean-stark trap, condenser, heating mantle, and thermometer. The synthesis was initiated by placing 30 grams of Jeffamine in the flask along with 4.74 grams of glycidol. The resulting mixture was heated to 30° C. During the resulting exotherm, the external heat source was removed. After ½ hour, 19.34 grams of 4-nitrobenzaldehyde was added in 200 ml. of toluene. The mixture was heated to reflux for two hours or until 2 ml. of water was recovered from the trap. The reaction product was then recovered and dried with sodium sulfate. The sodium sulfate was filtered off, and the toluene was removed by vacuum.

It was found that the material produced comprised a compound having both hydroxyl and Schiff base functionality. In addition, it was found that the material produced worked well as a propellant bonding agent. A stress v. strain curve for a propellant using this formulation, and other exemplary propellant formulations, is set forth in FIG. 1.

Examples 2

In this Example, a compound within the scope of the present invention was synthesized using the general procedure set forth in Example 1. The following materials in the following amounts were reacted:

| Material | Grams | Moles/Equiv. |
|---|---|---|
| Jeffamine T-403 | 30.00 | 0.1937 |
| glycidol | 4.79 | 0.0646 |
| benzaldehyde | 13.70 | 0.1291 |

The material produced has the following general structure:

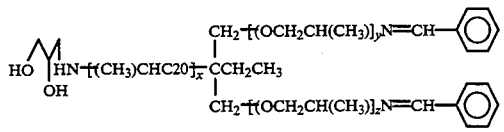

The compound produced resulted in markedly decreased amine content, and a resulting reduction in ammonia produced during propellant processing. Table I contains amine reduction data regarding this exemplary material.

TABLE I

| Bonding Agent | Active Amine Equiv. (/100 g) | % Amine Reduction |
|---|---|---|
| Tepanol (standard) | 1.28 | 0 |
| Example 2 | 0.14 | 89 |

Figure 2:
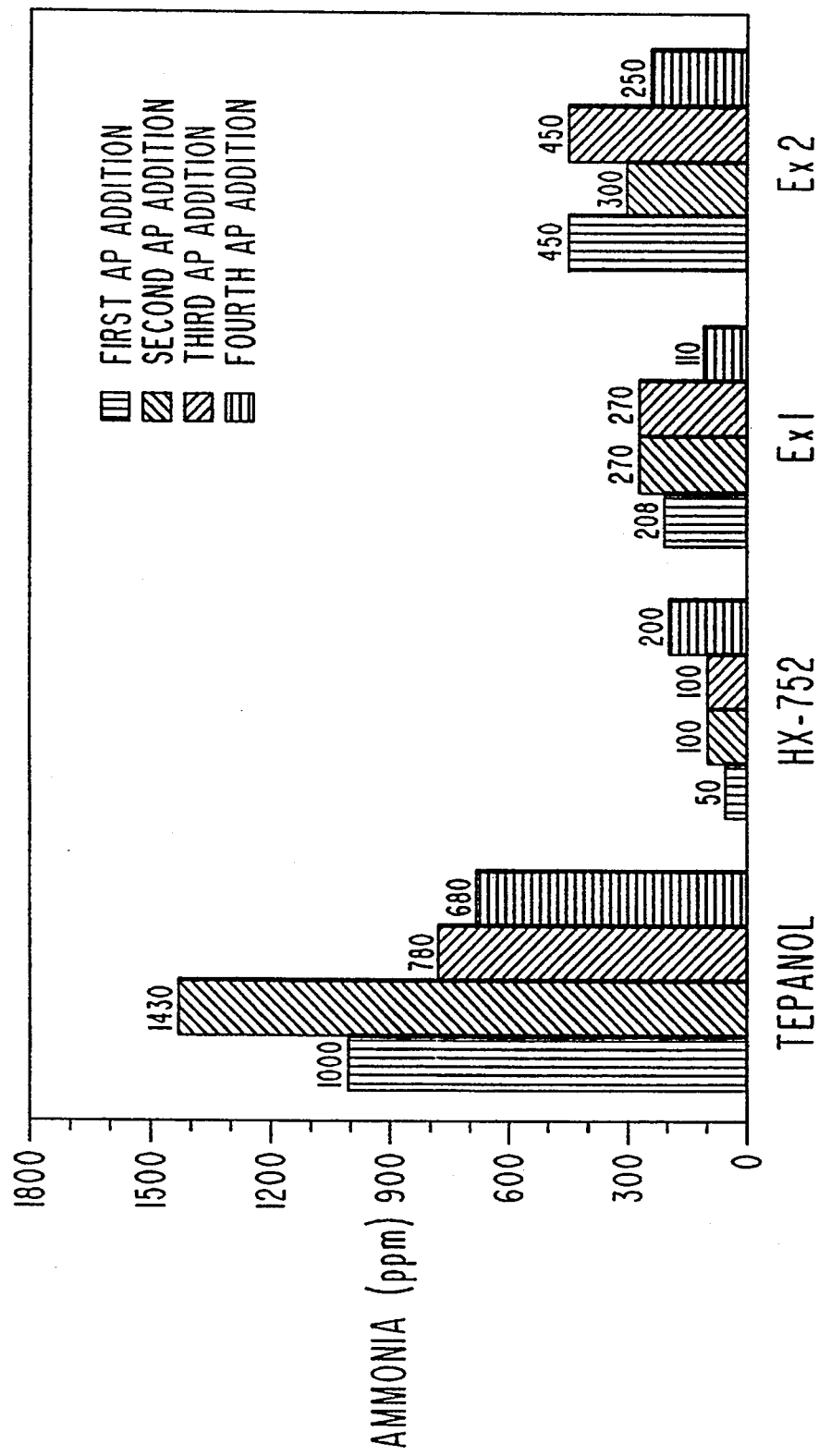
FIG. 2 is a bar graph which plots ammonia in parts per million for multiple samples.

In addition, FIG. 2 provides a graphical presentation of data regarding the production of ammonia during the formulation of a propellant using these exemplary materials as bonding agents. FIG. 2 illustrates the ammonia produced in parts per million in a one gallon mix. Data is recorded for the first through the fourth addition of ammonium perchlorate. Data is provided for propellants using Tepanol, HX-752, and with the bonding agents described in Examples 1 and 2 herein.

It can be seen from FIG. 2 that each of the propellants using the bonding agents of the present invention produced significantly less ammonia than the propellant using Tepanol. The propellants using these bonding agents experienced ammonia production more comparable to that experienced using the expensive HX-752 bonding agent.

Table II sets forth representative data regarding the processing properties of this compound. In Table II end of mix viscosity data is provided, along with ammonia concentration prior to curative addition.

TABLE II

| Bonding Agent | EOM VISC* | EOM VISC** | Amm. Conc. (ppm) |
|---|---|---|---|
| None | 12 | — | — |
| Tepanol | 7 | 2 | 680 |
| HX-752 | 11 | 6 | 200 |
| Example 1 | 14 | 9 | 110 |
| Example 2 | 9 | 9 | 250 |

*propellant made in 1-pint mixer
**propellant made in 1-gallon mixer

Thus, it can be seen that the processing characteristics of propellants employing the compounds falling within the scope of the present invention are comparable with propellants using conventional bonding agents.

Example 3

In this Example a propellant was formulated using a bonding agent within the scope of the present invention. The following materials were used in the following weight percentages:

| Material | Weight Percentage |
|---|---|
| R-45M (HTPB mfg. by ATOCHEM) | 12.09 |
| Bonding Agent (from Example 1 above) | 0.15 |
| Aluminum | 18.00 |
| Ammonium Perchlorate (200μ) | 48.30 |
| Ammonium Perchlorate (20μ) | 20.70 |
| Isophorone diisocyanate | 0.76 |

The propellant was formulated by conventional techniques. It was observed that the propellant had stress and strain measurements well within the acceptable range. Furthermore, only relatively small amounts of ammonia were released during processing.

SUMMARY

In summary, the present invention provides new organic compounds containing polyether Schiff base and hydroxyl functionality. These compounds are found to function well as bonding agents in the formulation of propellants. The present invention also provides propellants formulated employing the new compounds as bonding agents.

This group of compounds overcome some of the significant limitations encountered using conventional bonding agents. These materials do not produce significant quantities of ammonia during propellant formulation and are at the same time relatively inexpensive. These compounds are believed to provide both electrostatic coordination with ammonium perchlorate, and a degree of polymerization within the propellant matrix in order to bind particles while providing a processible material.

The data presented also clearly illustrates that when the bonding agents are used in a propellant, the propellant has good stress and strain characteristics. Thus, the propellants meet the objective mechanical criteria for use in actual practice.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An organic compound produced by the reaction of an amine and an aldehyde or ketone, and the further reaction with a material capable of imparting hydroxyl functionality to the organic compound, such that the ratio of C=N to hydroxyl in the compound is in the range of from about 1 to about 3, said compound comprising the following structure:

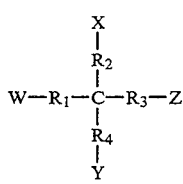

wherein $R_1$, $R_2$, $R_3$, and $R_4$ are the same or different and are selected from the group consisting of hydrogen and aliphatic linear or branched alkyls having from 1 to 20 carbon atoms, wherein among $R_1$, $R_2$, $R_3$, and $R_4$ there are at least two ether linkages between aliphatic residues, wherein at least one of $R_1$, $R_2$, $R_3$, and $R_4$ contains a hydroxyl group, wherein at least one of $R_1$, $R_2$, $R_3$, and $R_4$ contains a Schiff base, wherein the only interruptions in the chains comprising $R_1$, $R_2$, $R_3$, and $R_4$ are, O, N, or Schiff base, wherein W, X, Y, and Z are selected from the group consisting of free hydroxyl,

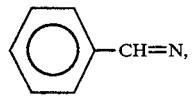

H, or $CH_3$, and wherein in the event one or more of $R_1$, $R_2$, $R_3$, and $R_4$ is H then the corresponding W, X, Y, or Z is deleted from the structure.

2. An organic compound as defined in claim 1 wherein at least one of W, X, Y, or Z comprises hydroxyl.

3. An organic compound as defined in claim 1 wherein at least one of W, X, Y, or Z comprises Schiff base.

4. An organic compound as defined in claim 1 wherein said compound has at least one aromatic functional residue.

5. An organic compound as defined in claim 1 wherein said organic molecule has at least two Schiff bases.

6. An organic compound as defined in claim 1 wherein said amine is selected from the group consisting of molecules having multiple amine functionality.

7. An organic compound as defined in claim 1 wherein said aldehyde is selected from the group consisting of p-nitrobenzaldehyde and benzaldehyde.

8. An organic compound as defined in claim 1 produced by the further reaction of the amine with an epoxide having at least one hydroxyl group.

9. An organic compound having the following structure:

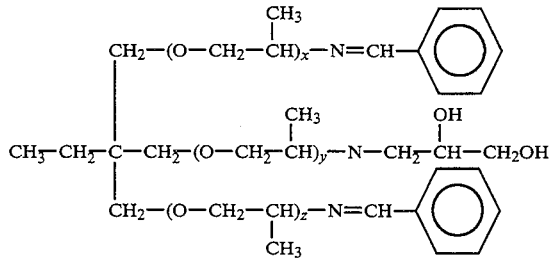

wherein the sum of $X+Y+Z$ is in the range of 0 to 100.

* * * * *